United States Patent
Murphy et al.

[11] Patent Number: 5,772,971
[45] Date of Patent: Jun. 30, 1998

[54] IODINE-BASED MICROBIAL DECONTAMINATION SYSTEM

[75] Inventors: Joseph Murphy, Northbridge; John Hickey, Weymouth; Yongjun Duan, Lexington, all of Mass.

[73] Assignee: Symbollon Corporation, Framingham, Mass.

[21] Appl. No.: 677,366

[22] Filed: Jul. 5, 1996

[51] Int. Cl.[6] .................................................. A61L 2/00
[52] U.S. Cl. ........................... 422/292; 422/28; 422/108; 422/110; 422/111
[58] Field of Search ................................... 422/28; 7/292, 7/307, 108, 110, 111, 82.09, 82.02; 250/455.11

[56] References Cited

U.S. PATENT DOCUMENTS

| | | | |
|---|---|---|---|
| 3,215,627 | 11/1965 | Tools | 210/62 |
| 3,232,869 | 2/1966 | Gard | 210/62 |
| 4,012,199 | 3/1977 | Luger | 422/62 |
| 4,892,706 | 1/1990 | Kralovic | 422/28 |
| 5,091,343 | 2/1992 | Schneider et al. | 422/297 |
| 5,217,698 | 6/1993 | Siegel et al. | 422/295 |
| 5,225,160 | 7/1993 | Sanford et al. | 422/28 |
| 5,441,611 | 8/1995 | Laufenberg et al. | 205/778.5 |

FOREIGN PATENT DOCUMENTS 840971  5/1970  Canada.

Primary Examiner—Timothy McMahon
Assistant Examiner—Alex Noguerola

[57] ABSTRACT

A microbial decontamination system includes a chamber for housing items to be decontaminated as well as a source of one or more iodine-containing fluids that are conveyed to the chamber as necessary. The system also includes a detector element for monitoring the concentration of free iodine within the chamber. A signal representative of the free iodine concentration is conveyed to a controller element which communicates with receptacles for housing the iodine-containing fluids so that additional iodine-containing fluids may be added to maintain the free iodine concentration within the chamber at a desired level.

10 Claims, 1 Drawing Sheet

IODINE-BASED MICROBIAL DECONTAMINATION SYSTEM

BACKGROUND OF THE INVENTION

The present invention relates to systems and apparatuses for sterilizing and/or disinfecting items such as medical and surgical instruments and devices. More particularly, the invention relates to such systems and apparatuses that utilize iodine-based disinfectants and sterilants.

The term "disinfection" refers to the elimination of pathogens from an item or instrument. Sterilization refers to the absence of all life forms, including dehydrated spores, from an item or instrument. The term "decontamination" as used herein generically is intended to encompass disinfection, high level disinfection and/or sterilization.

Many medical instruments and devices are reusable. Such equipment must be carefully sterilized and disinfected after each use to prevent the spread of disease and infection. A common and often effective sterilization technique employs the use of heat and pressure, usually in an autoclave, to kill pathogens and other infectious agents. However, some medical instruments are heat sensitive and are not able to be subjected to heat sterilization techniques.

Some medical devices which are not able to withstand the rigors of heat decontamination are sterilized using a gas such as ethylene oxide. This decontamination method is not always favored because ethylene oxide based decontamination systems tend to be expensive and pose the added drawbacks of toxicity and volatility.

Liquid decontamination systems use strong oxidants that can be corrosive. The preparation and use of these systems is labor intensive. The compounds must be prepared prior to use, due to their typically short shelf life, and careful rinsing is required to remove any residue. The process of rinsing items after the decontamination process can itself contribute to subsequent contamination of items.

One known technique for chemically sterilizing and/or disinfecting medical devices is the use of a highly concentrated iodine solution, having free molecular iodine at a concentration of about 0.5 to 20% by weight. These systems can be used in concentrated form or diluted with water prior to use in the range of about 1:100 to 1:1000. Typically, these compositions contain a level of total iodine that is much higher than the minimum iodine concentration required for biocidal efficacy. These high levels of iodine are necessary to achieve adequate product stability since a free molecular iodine concentration rapidly decreases over time. One drawback of such compositions is that the use of such high concentrations of iodine contributes to undesirable toxicological problems and unwanted interactions with inanimate materials. For example, such high concentrations of iodine can result in the staining of instruments and other materials that are contacted by the iodine composition.

The use of liquid sterilization systems has other drawbacks as well. Typically, a technician must prepare a liquid sterilant composition and manually immerse the items to be decontaminated for a desired time period. Clearly, the high degree of manual labor as required for such sterilization techniques can decrease the utility and efficacy of the technique.

In an attempt to overcome some of the drawbacks associated with manual decontamination systems, there have been proposed automated and/or semi-automated decontamination systems. Examples of such systems are disclosed in U.S. Pat. Nos. 5,217,698; 4,892,706; 5,225,160; and 5,091,343. Many of these systems rely upon a peracetic acid active composition that is typically formed by reaction during the decontamination process. Peracetic acid is corrosive and toxic, and requires careful handling and washing of instruments after decontamination.

Accordingly, there is a need for more convenient and effective automated and semi-automated chemically-based instrument decontamination systems that utilize iodine-based decontamination compounds and compositions.

It is thus an object of the invention to provide automated/semi-automated decontamination systems that can pass the Association of Official Analytical Chemists (AOAC) Sporocidal Assay by chemical means using free molecular iodine as the active agent. It is also an object to provide such a system that is capable of using low but effective concentrations of iodine. A further object is to provide such a system that monitors and adjusts the concentration of free iodine to maintain an effective but non-excessive level of iodine within the system. These and other objects will be apparent to one having ordinary skill in the art upon reading the disclosure that follows.

SUMMARY OF THE INVENTION

The Food and Drug Administration (hereinafter referred to as the "FDA") regulates disinfection and sterilization of medical equipment; the Agency has defined "liquid germicides" by a set series of efficacy tests. Liquid germicides are only recommended for use on medical equipment when sterilization by heat is not possible. A liquid germicide must inactivate dehydrated spores using the Association of Official Analytical Chemists (AOAC) Sporocidal Assay within the contact time identified on its label in order to be termed a sterilant. Surprisingly, the Agency requires a liquid germicide to inactivate dehydrated spores within some contact time (not the contact time identified on its label) in order to be termed a high level disinfectant. Hospitals minimally require high level disinfection of medical devices prior to reuse.

Iodine compositions are not known to pass the AOAC Sporocidal Assay. In fact, none of the commercially available iodine biocides currently availalbe will pass the AOAC Sporocidal Assay. There are no literature reports that demonstrate the ability of an iodine-based biocide to pass the AOAC Sporocidal Assay. None of these compositions can pass the AOAC Sporocidal Assay at temperatures close to room temperature.

Iodine compositions that contain total iodine concentrations of up to 1,000 ppm and saturated levels of free molecular iodine have not been capable of passing the AOAC Sporocidal Assay. The present invention discloses the fact that it is possible to pass the AOAC Sporocidal Assay using very low concentrations of iodine; in fact, it is possible to pass the AOAC Sporocidal Assay using concentrations of active iodine that are at 10 parts per million. In order to be successful in the AOAC Sporocidal Assasy with iodine-based biocicdes it is necessary to deliver a steady concentration of low levels of active iodine throughout the test procedure. It is not understood why a constant low level of iodine works over a prolonged time period while an equivalent amount of unreplenished iodine at elevated concentrations does not.

The present invention provides a decontamination system that makes it possible to sterilize or disinfect medical devices and medical instruments through chemical means. The system comprises a decontamination chamber that houses the items to be decontaminated, and a source of an iodine-containing fluid. The system also includes elements such as pumps, valves and conduits for communicating the iodine-containing fluid to the decontamination chamber. Further, the system includes a detector element that determines the concentration of free iodine within the iodine-containing fluid housed in the decontamination chamber. In response to the detection element, the system regulates the concentration of free iodine within the iodine-containing fluid, present in the decontamination chamber, to maintain the concentration of free iodine within a an effective range of 15 to 150 parts per million at a low level rate of iodine replenishment. The system may also include a source of a rinse fluid which can be selectively communicated to the decontamination chamber at a desired time. Preferably, the chamber also includes one or more valve elements that enable fluid to be drained from or retained within the chamber.

A controller element preferably is in electrical communication with the various elements of the system, including the detector, the source of iodine containing fluid, and various valves and pumps. The controller preferably will receive signals relating to the concentration of iodine within the decontamination chamber and in response to such signals, will send signals to the various elements of the system to facilitate and regulate the timing and sequence of events that form the contamination process.

The iodine containing fluid useful with the contamination system of the invention comprises free iodine, compounds that react to form free iodine, or a combination of free iodine and iodine forming compounds. Preferably, the iodine forming compounds include a slow oxidant and an iodide salt.

Various detection elements can be used to assess the concentration of free iodine within the chamber. Such systems include spectrophotometers and potentiometers configured to selectively measure iodine concentration. Preferably, the detection element is in electrical communication with a controller.

DETAILED DESCRIPTION OF THE INVENTION

Figure 1:
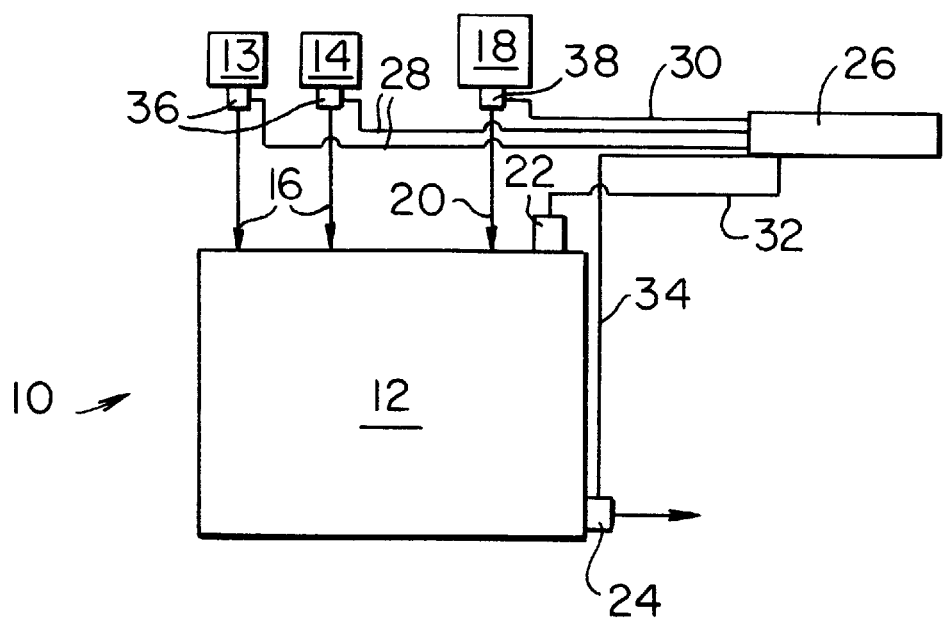
FIG. 1 systematically illustrates an iodine-based disinfecting system according to the present invention.

For convenience, certain terms employed in the specification, examples, and appended claims are defined below. The term "AOAC Sporocidal Assay", as used herein, refers to a microbiological test method descrbed in section 966.04 on page 141 in the book entitled *Official Methods of Analysis of the Association of Official Analytical Chemists,* fifteenth edition, 1990 which is published by the Association of Official Analytical Chemists, Inc., who are located in Arlington, Va.

The term "thiosulfate titrable iodine" or "total iodine" is a term of art, and, as used herein, refers to iodine species which can be titrated by thiosulfate. Total iodine includes free molecular iodine and triiodide, since they are both titrated by sodium thiosulfate.

The terms "slow oxidant" or "slow oxidizer," as used herein, refer to an agent that can oxidize iodide anion to molecular iodine over an extended period of time, in contrast to "fast" oxidants which rapidly and quantitatively oxidize iodide to iodine. For example, the oxidation of iodide by a slow oxidant such as persulfate occurs over a period of hours or days.

The terms "source of persulfate anion" or "persulfate salt," as used herein, refer to any material alone or in combination which can serve as a precursor for persulfate anion. Persulfates are also known as "peroxydisulfates." Sources of persulfate anion include sodium persulfate, ammonium persulfate and potassium persulfate.

The term "iodine species ratio," as used herein, refers to the ratio of free molecular iodine ($I_2$) to other iodine species such as iodide and triiodide.

The term "iodide salt" refers to any salt of the iodide anion which yields the iodide anion when dissolved in an aqueous medium. Suitable counterions for the iodide anion include sodium, potassium, calcium, and the like, as well as ammonium cations.

A "source of initial free molecular iodine" or "initial-iodine source," as used herein, refers to a source of iodine that rapidly generates a selected concentration of molecular iodine. For example, molecular iodine, when added to a composition, immediately generates a selected concentration of free molecular iodine in solution. Other sources of initial iodine include iodophores, and combinations of iodide anion with a fast oxidant.

Below a pH of 7.0, iodine atoms assume three principal forms. These three forms are triiodide, iodide and free molecular iodine, of these three species, only free molecular iodine is biocidal. At a pH of 7.0 and above, hypoiodous acid is formed in substantial concentrations. Hypoiodous acid is biocidal but its biocidal activity is substantially less than free molecular iodine on a molar basis. Additionally, hypoiodous acid is subject to hydrolysis and has limited stability in an aqueous environment.

Free molecular iodine is lost from an aqueous medium in several ways. Free molecular iodine is hydrated by water and, in an aqueous system, undergoes hydrolysis through a complicated series of reactions that can be summarized in the following two equations:

$$I_2 + H_2O = HOI + I^- + H^+ \qquad (1)$$

$$3HOI = IO_3^- + 2I^{-1} \qquad (2)$$

The hydrolysis products—iodate ($IO_3^-$) and iodide ($I^-$)—have no significant antibacterial activity. Elevated or basic pH values speed up iodine hydrolysis by consuming the protons formed by hydrolysis of elemental iodine. When the pH of a solution is equal to or greater than 7, iodine is hydrolyzed very rapidly. In contrast, iodine is hydrolyzed slowly when the pH is 6 or lower. A preferred pH range for decontamination with iodine-containing solutions is about 2 to about 5, more preferably about 3 to about 5.

Free molecular iodine also evaporates considerably more rapidly than either iodide or triiodide, and, in the absence of organic matter and reducing agents, evaporation constitutes a major source of overall iodine loss in aqueous systems that freely exchange with the environment. Finally, free molecular iodine reacts with organic matter and is consumed as a result of this reaction.

Therefore, it is necessary for an effective iodine-containing germicidal solution to continuously replace the free molecular iodine that is lost through the pathways described above. One aspect of the present invention is based, at least in part, on the observation that persulfates slowly oxidize iodide anions into free molecular iodine in an aqueous medium. The continuous slow oxidation of iodide to iodine provides a source of iodine which is effective to maintain germicidal activity of a solution over an extended period of time.

This iodine-based decontamination composition is of use by itself. However, the invention further provides a system that, on an automated or semi-automated basis, utilizes the iodine-based composition to decontaminate items, such as medical instruments and devices, in an effective and efficient manner. The minimum concentration of total iodine contemplated under this invention is 15 ppm and the maximum concentration is 150 ppm. The rate at which free molecular iodine is replaced or provided to the germicide compositions under this invention is between 0.5 ppm per hour and 25 ppm per hour.

As illustrated in the FIGURE, the decontamination system of the invention comprises a chamber 12 for housing instruments and/or devices to be decontaminated, and one or more sources of an iodine-containing fluid 14 which can communicate with chamber 12 through conduits 16. Optionally, a source of a rinse fluid 18 may also be present. The rinse fluid preferably is communicated through conduit 20 to chamber 12. One or more valves 36, 38 may be present to selectively control the flow of fluids into chamber 12. A valve 24 may also be present in the system, preferably at a bottom portion of the chamber, to drain any fluids from within the chamber 12. Valves 24, 36, 38 may be manually or electronically actuated.

The system also includes a detector element 22 that determines the free iodine concentration within the chamber 12. Preferably, detector 22 communicates electrically with controller 26 through wire 32.

Optionally, the chamber may be equipped with a heating source (not shown) and an agitation device (not shown).

A controller element 26 preferably forms part of the system 10 to regulate and facilitate the sequence of events that represent the decontamination process. The controller 26 preferably communicates electrically, through wires 28 with valves 36 associated with the source of iodine containing fluid 14, through wire 30 with valve 38 associated with rinse fluid source 18, and through wire 34 with valve 24 associated with decontamination chamber 12.

The disinfection chamber 12 is preferably dimensioned to accept a wide variety of medical devices ranging in size from small, hand held tools to larger devices such as endoscopes and similar instruments. The chamber 12 preferably has an access port (not shown) that can be opened and closed in order to facilitate access to the chamber. The chamber may have an open top, but preferably it is closed during operation in order to minimize evaporation and the consequent loss of free iodine.

Selectively operable valves preferably are associated with the iodine-containing fluid source and the rinse fluid source to control the delivery of such fluids to decontamination chamber 12. A valve 24 is also associated with the decontamination chamber 12 in order to effect drainage of the contents of the chamber. The valves may be manually operable, but preferably they are selectively opened and closed in response to signals transmitted by controller 26. One or more pumping mechanisms (not shown) may be associated with the valves and/or the flow conduits associated with the valves to effect delivery of fluid to chamber 12. Valve 24 may also have associated therewith a pump (not shown) to facilitate rapid drainage of chamber 12. Any pumps present in the system may also be actuable by signals conveyed by controller 26.

One of ordinary skill in the art will readily appreciate that any one of a variety of controllers may be used with the invention. As noted above, the controller should be in electrical communication with detector 22 in order to receive periodically generated signals representative of free iodine concentration within chamber 12. The controller is a conventioinal comparator which compares such signals to information stored within the controller that is representative of a desired range for the iodine concentration.

The controller is also in electrical communication with valves and/or pumps to regulate the flow of fluids into and out of chamber 12. If the signal provided from detector 22 reveals that the free iodine concentration is less than the desired range, the controller activates one or more of the valves and/or pumps associated with the iodine-containing fluid sources to add additional iodine-containing fluid to chamber 12.

Detector 22 is a conventional instrument, preferably an instrument disposed within chamber 12 or disposed in contact with fluid held in chamber 12 that is able to determine the free iodine concentration of fluid within the chamber. The detector should be able to make multiple readings of the free iodine concentration, within a specified time period. For example, the detector can preferably make at least 1 to 10 readings per second. The detector should also be able to communicate signals representative of free iodine concentration to the controller element. One of ordinary skill in the art will appreciate that a number of devices may suitably serve as detectors. For example, the detector may be a spectrophotometer or a potentiometer. In an exemplary embodiment, the iodine content of the iodine-containing fluid is determined by monitoring absorbance due to free iodine, e.g., at about 450 nm. Alternatively, aliquots of the iodine-containing fluid can be reacted with a reagent, e.g., starch, and the absorbance due to the starch-iodine complex is measured spectrophotometrically, according to known methods. Potentiometric detection of free iodine is also known in the art, see, e.g., W. Gottardi (1983) *Fresenius Z. Anal. Chem.* 314:582–585.

The sources of iodine-containing fluid may be maintained in one or more receptacles, preferably closed receptacles, that are in fluid communication with chamber 12 via conduits 16. The desired fluids can be maintained within these receptacles until they must be conveyed to chamber 12, as noted above. Similarly, the source of rinse fluid is a receptacle, preferably closed, that houses a suitable rinse fluid such as sterilized water. As the source of rinse fluid 18 is also in fluid communication with chamber 12, the rinse fluid can be conveyed to chamber 12 as necessary in the manner described above.

As noted above, the invention also provides an iodine-containing fluid which serves as a decontaminating composition for generating free molecular iodine. The composition comprises a persulfate salt; an iodide salt present in molar excess over the persulfate salt; and an aqueous medium having a pH less than or equal to about 6.5. The composition is effective, upon combining the persulfate salt and the iodide salt, in the aqueous medium, to generate free molecular iodine that is present at a concentration of at least 10 ppm out of a minimum total iodine concentration ofabout 20 ppm. In certain embodiments, the composition further includes an initial source of iodine. Preferably, the concentration of free molecular iodine is maintained at least about 15 to 30 ppm out of a total iodine concentration of about 50 ppm.

In one embodiment the iodide salt and the persulfate salt may be provided in separate receptacles. In this embodiment, a solution of iodide salt and a solution of persulfate salt can be separately conveyed to chamber 12, and, upon mixing in the chamber, react to provide an iodine-containing fluid; or, alternatively, a solution of iodide salt and a solution of persulfate salt can be mixed, e.g., at a mixing tee (not shown) joining conduits 16, to provide an iodine-containing fluid which is then conveyed to the chamber 12. Various additives, including buffers, surfactants detergents, dyes, perfumes, humectants, emollients, iodine sequestrants, anti-foaming agents and anti-corrosive agents, may also be included within one or both of the receptacles 14. The selection of suitable additives will be routine to the skilled artisan. Optionally, an initial source of free molecular iodine can be in the form of crystals or a concentrated iodine solution and provided in a separate receptacle (not shown). An initial free molecular iodine source is sometimes useful where immediate iodine-derived germicidal activity is desired since it normally requires approximately 30 minutes, depending on the reaction conditions, for reaction between iodide and persulfate salts to generate germicidally-active levels of free molecular iodine. In an illustrative embodiment, a peroxidase and a source of peroxide can be used to rapidly generate initial iodine. In another embodiment, an iodophor such as Povidone can provide free iodine during an initial reaction period. In yet another embodiment, a small amount of persulfate can be activated by a promoter, e.g., a metal. For example, addition of a small amount (e.g., 5 mole %) of copper can activate a small amount of persulfate (e.g., 5 mole %). The "activated" persulfate rapidly oxidizes iodide anion to molecular iodine, the copper and "activated" persulfate are consumed. The slow oxidation of iodide by persulfate then continuously generates free molecular iodine over an extended period.

In another embodiment, the iodine-containing fluid can be provided by contacting a solution of an iodine salt with a rapid oxidant. Exemplary rapid oxidants include hydrogen peroxide, which produces no toxic by-products upon reaction with iodide. Alternatively, an iodide-containing fluid can be contacted with a solid-phase oxidizing agent, and the resulting iodine-containing fluid separated and conveyed to the chamber 12. For example, a flow column containing solid granules with immobilized zirconium peroxide (see, e.g., U.S. Pat. No. 5,464,603) (not shown) can be disposed between the chamber 12 and a receptacle of iodide-containing fluid. As the iodide-containing fluid passes through the flow column, free iodine is produced and conveyed to chamber 12, while the solid particles are retained in the column.

In another embodiment, the iodine-containing fluid can be provided by passing an iodide-containing solution through a packed bed electrolytic reactor (not shown) disposed between the chamber 12 and a receptacle of iodide-containing fluid, e.g., according to the method described in U.S. Pat. No. 5,419,816.

EXAMPLE 1

An endoscope is placed in the chamber 12 and the controller 26 is programmed to begin the decontamination cycle. An iodide-containing solution in receptacle 14 is pumped through valve 36 to a mixing tee (not shown), where the iodide-containing solution is mixed with a solution of a persulfate salt from a separate receptacle 14. The combined solution is then conveyed to chamber 12, where it is pumped or sprayed over the instrument to be decontaminated. The iodine-containing solution drains by gravity to the bottom of the chamber 12, where it accumulates, preferably at least partially submerging the instrument in the disinfecting solution. When sufficient iodine-containing fluid has been conveyed to the chamber, valves 36 are closed in response to signals from controller 26.

Decontamination proceeds for a predetermined time period, preferably with agitation of the fluid in chamber 12. Detector element 22 determines the free iodine concentration in chamber 12, and controller 26 compares signals from detector 22 to stored pre-established values. When the free iodine concentration falls below a preset value, additional reagents are added to the chamber 12 from receptacles 14 in response to signals from the controller 26.

When the preset decontamination time is reached, the valve 24 is opened and the iodine-containing fluid is drained from the chamber 12. The valve 24 is closed, and valve 38 is opened to convey sterile rinse fluid through conduit 20 to chamber 12, and the instrument in chamber 12 is rinsed with rinse fluid. When rinsing is complete, valve 24 is again opened and the rinse fluid is drained from the chamber. The decontaminated endoscope is then removed from the chamber.

EXAMPLE 2

An iodine composition was formulated that was suitable for sporocidal assay under AOAC methods. To make a claim as a sterilant or a sporocide with the FDA a germicide product in the United States must pass the Association of Official Analytical Chemists sporocidal activity test (AOAC sporocidal assay).

To a pH 4.5 solution buffered with sodium citrate and containing 20 ppm initial titrable iodine with 10 ppm as free molecular iodine, sodium persulfate was added to a concentration of 0.07%. The initial iodine concentration was achieved by addition of iodine crystals. The addition of sodium persulfate resulted in the controlled generation of free molecular iodine at a rate that was equal to about 4 ppm over the course of the first 24 hours. The disinfection solution was tested according to the AOAC sporocidal method and the composition killed all of the vacuum dried *Bacillus subtilis* spores that were coated on 60 porcelain penicylinders in 18 hours at 30° C. The identical experiment was repeated using *Bacillus subtilis* spores coated onto Dacron sutures at 20° C. No failures were found when testing this solution against *Bacillus subtilis* spores coated on 5 Dacron sutures in 5 days at 20° C.

Those of ordinary skill in the art will recognize, or be able to ascertain using no more than routine experimentation, numerous equivalents to the specific procedures and systems described herein. Such equivalents are considered to be within the scope of the invention and are covered by the following claims. The contents of all references and patent applications described herein are hereby incorporated by reference.

What is claimed is:

1. Biocidal iodine-based decontamination apparatus having a decontamination chamber for sterilizing or disinfecting medical devices and/or instrumentation by contact with free molecular iodine, said apparatus comprising:

a source of iodine forming liquid reagents which generate free molecular iodine in situ upon admixture with water;

supply means for feeding said iodine forming liquid reagents into said decontamination chamber in or with an aqueous medium such that free molecular iodine is generated in situ, in said apparatus, at a rate that is no less than 0.5 ppm per hour and no more than 25 ppm per hour; and control means for maintaining the concentration level of said generated free molecular iodine above a minimum level of about 15 ppm over a prolonged time period, said control means comprising;

detection means for determining the concentration level of free molecular iodine within said decontamination chamber; and controller means responsive to said detection means for comparing the detected level of free molecular iodine in said decontamination chamber to information representative of said minimum concentration level and said flow rate information for regulating said supply means in accordance therewith.

2. The decontamination apparatus of claim 1 further comprising a supplemental source of free iodine connected to said supply means.

3. The decontamination apparatus of claim 1 wherein said iodine forming liquid reagents comprise an iodide salt and an oxidant selected from the group consisting of a source of persulfate anion and/or a peroxide.

4. The decontamination apparatus of claim 3 wherein said iodide salt is selected from the group consisting of sodium iodide, potassium iodide and calcium iodide.

5. The decontamination apparatus of claim 4 wherein said source of persulfate anion is selected from the group of sodium persulfate, ammonium persulfate and potassium persulfate with said iodide salt being in molar excess over said persulfate source.

6. The decontamination apparatus of claim 5 further comprising means for combining said iodide salt and said oxidant with said aqueous medium prior to delivery to said decontamination chamber.

7. The decontamination apparatus of claim 5 further comprising means for maintaining said iodide salt and said oxidant in separate solutions at least one of which is an aqueous solution with said supply means comprising conduit means for separately feeding each of said solutions to said decontamination chamber.

8. The decontamination apparatus of claim 7 wherein said control means further comprises valve means for metering the supply of iodine forming liquid reagents to said decontamination chamber.

9. The decontamination apparatus of claim 8 wherein said detection means comprises a spectrophotometer.

10. The decontamination apparatus of claim 8 wherein said detection means comprises a potentiometer.

\* \* \* \* \*